(12) United States Patent
Collura (10) Patent No.: US 7,269,456 B2
(45) Date of Patent: Sep. 11, 2007

(54) REPETITIVE VISUAL STIMULATION TO EEG NEUROFEEDBACK PROTOCOLS

(76) Inventor: Thomas F. Collura, BrainMaster Technologies, Inc. 24490 Broadway Ave., #2, Oakwood Village, OH (US) 44146

( * ) Notice: Subject to any disclaimer, the term of this patent is extended or adjusted under 35 U.S.C. 154(b) by 583 days.

(21) Appl. No.: 10/158,299

(22) Filed: May 30, 2002

(65) Prior Publication Data
US 2003/0225340 A1  Dec. 4, 2003

(51) Int. Cl.
A61B 5/04  (2006.01)
(52) U.S. Cl. .................. 600/545; 600/544; 128/905
(58) Field of Classification Search .............. 600/545, 600/544; 128/905
See application file for complete search history.

(56) References Cited

U.S. PATENT DOCUMENTS

| | | | | |
|---|---|---|---|---|
| 4,421,122 | A | * | 12/1983 | Duffy ..................... 600/544 |
| 4,739,772 | A | * | 4/1988 | Hokanson et al. .......... 600/544 |
| 4,955,388 | A | * | 9/1990 | Silberstein ............... 600/544 |
| 5,331,969 | A | * | 7/1994 | Silberstein ............... 600/544 |
| 5,365,939 | A | * | 11/1994 | Ochs ...................... 600/545 |
| RE36,348 | E | | 10/1999 | Carter et al. |
| 6,081,743 | A | * | 6/2000 | Carter et al. ............. 600/544 |
| 2004/0097802 | A1 | * | 5/2004 | Cohen .................... 600/411 |

OTHER PUBLICATIONS

T.F. Collura & R.J. Lorig, "Real-Time Filtering of Transient Visual Evoked Potentials"; 30th ACEMB, Los Angeles Hilton, Los Angeles, California Nov. 5-9, 1977.

T.F. Collura, "Real-Time Evoked Potential Correlates of Directed Attention"; 31st ACEMB, Marriott Hotel, Atlanta, Georgia, Oct. 21-25, 1978.

T.F. Collura, "A Transient-Event Model for EEG Power Spectra"; 40th ACEMB, Niagara Falls, NY, 1987, Annual Conference on Engineering in Medicine and Biology.

Thomas F. Collura, "Real-Time Filtering for the Estimation of Steady-State Visual Evoked Brain Potentials", IEEE Trans. on Biomedical Eng., vol. 37, No. 6, Jun. 1990.

Thomas F. Collura, "Human Steady-State Visual and Auditory Evoked Potential Components During a Selective Discrimination Task", Journal of Neurotherapy 1996.

* cited by examiner

Primary Examiner—Charles A. Marmor, II
Assistant Examiner—Navin Natnithithadha
(74) Attorney, Agent, or Firm—Roetzel & Andress (57) ABSTRACT

An EEG neurofeedback and total evoked brain activity measurement methods utilize minimum ambient EEG activity as stimulant frequencies. A method of using repetitive stimulation in conjunction with EEG neurofeedback protocols is described. Electrodes, attached to a subject's scalp, transmit electroencephalographic (EEG) signals from the subject. These signals are in response to the visual and/or auditory stimuli being displayed to the subject. The resultant EEG signals are then filtered at pre-defined frequencies or frequency bands. The output from the filtered EEG signals is then analyzed and monitored for short-term state changes. The invention also uses flicker stimulation, real-time signal filtration and feedback, feedback during audio and visual stimulation derived from filtered outputs, and fundamental and integral harmonics in combination with total evoked response.

12 Claims, 7 Drawing Sheets

REPETITIVE VISUAL STIMULATION TO EEG NEUROFEEDBACK PROTOCOLS

FILED OF THE INVENTION

The present invention relates generally to a method for studying dynamic sensory brain processes, and more particularly, to a method for using repetitive visual and/or auditory stimulation in the context of EEG neurofeedback protocols.

BACKGROUND OF THE INVENTION

The origin and nature of brain waves as measured from the human scalp has been a topic of ongoing research. For example, the electroencephalogram (EEG) as measured from the intact human scalp is of interest in psychology and psychophysics because it can provide an indication of the activity of brain cells in the awake, alert state. Of particular use are the minute potentials evoked by sensory stimuli, for these time-locked transient wavelets show how populations of cells behave in response to afferent volleys carried by primary sensory fibers.

Whenever a brief stimulus is presented to a trainee, there is a transient brain response due to that stimulation. The signal produced in the EEG is generally very small, but it can be detected. In cases where it is possible to discern the EEG changes, either in the raw EEG or in a processed form, then there is said to be an "event-related potential" (ERP), or a "sensory evoked potential" (SEP). The evoked potential (EP) provides an indication of the effect of the stimulus on the brain, and it has been established that the EP is sensitive to changes in sensory and perceptual processes.

When muscle and eye movements are minimized by relaxation, the predominant sources of scalp potential are populations of cells in the brain, with large cortical cells providing the majority of the voltage. Due to the distribution of ions across active membranes, each cell tends to take on dipole characteristics and produce potentials which are carried to the scalp by volume conduction. When cells polarize in asynchrony, the net surface potential is small due to the cancellation of out-of-phase components. The presence of a measurable surface potential thus depends on the fact that some cells are polarizing in synchrony, generally in response to an afferent volley in which fibers are firing in unison.

Stimulation may be repetitive, or it may be non-repetitive. By repetitive, we mean that successive stimuli occur within a relatively short interval of time (e.g., less than one second), they occur at regular intervals, and that they are sustained throughout the stimulation period, which can be anywhere from under a second, to many minutes, or longer. When the stimulation is not repetitive, then it is said that there is a single EEG brain evoked potential response that is embedded in the ongoing EEG activity.

When a single brief stimulus is presented to the nervous system, the response generally consists of a single time-limited pattern, or burst, of action potentials carried along the appropriate afferent pathway. In the case of a light flash, the optic nerve carries the impulses; in the case of a click, the auditory nerve is involved. In both cases, sensory fibers first synapse at lower brain centers; second, third, and higher-order fibers then carry a volley of processed information to the appropriate sensory cortex. The cortical response in both modalities consists of a time-limited sequence of processing steps involving various areas of the brain; there is a substantial amount of information exchange or "crosstalk" between cortical centers, with pathways including lower brain areas. A sufficient number of cells are involved in these processes to give rise to measurable transient surface waves, the evoked potentials. Some evoked potential waves appear to involve predominantly localized cortical areas, others result from activity over widespread locations.

If the stimuli are provided in a successive manner so that a computer can analyze more than one of them, it is possible to extract an estimate of the averaged evoked potential, which represents a canonical, or standard, response of the brain, to the stimuli. When the stimulation is repetitive in nature, each stimulus follows the previous one by a short period of time (less than 500 milliseconds), and the successive evoked responses in the brain are found to overlap in time, so that the trailing end of one response is superimposed upon the beginning of the next.

When repetitive stimulation is applied, there is a small periodic signal introduced in the EEG. In general, a repetitive flash produces an EEG response at the same frequency as the stimulation, and harmonics may be present. When sinusoidal light is applied, there is a stabilizing effect, and an interaction with intrinsic rhythms. This is not seen in the case of flickering or square-wave light, which produces a simple train of stimulus-induced visual evoked potential waves.

Generally, steady-state evoked potentials are understood in terms of nonlinear mechanisms which involve both "driving" phenomena and the production of harmonics from a pure sinusoidal input. According to this interpretation, the evoked response is said to be nonlinear because of the presence of higher-order harmonics, plus the appearance of "resonance" phenomena observed near the alpha frequency.

However, an alternative interpretation is possible when study is limited to the responses to discrete stimuli such as brief clicks or flashes. In this case, a predominant mechanism leading to the evoked response is the linear superposition of successive discrete responses, to produce a complex periodic wave. This will be valid as long as successive stimuli arrive at intervals large enough for the recovery function to be near 100%, typically 100 msec or more.

For example, the waveforms of averaged visual evoked response elicited by spot flashes from 0.5 per second to 15 per second was visually inspected to confirm that the size and latency of evoked potential components is preserved across frequencies, and that the successive responses overlap, producing the observed response. Furthermore, the synchronous component response shown is identical in shape to the frequency spectrum of single evoked responses. This similarity in spectral energy distribution is what would be expected from a linear overlap model. In particular, a low-frequency band from 4 to 10 Hz is evident, and a higher-frequency band from 12 to 20 Hz is also evident. From these results, it is clear that repetitive visual stimulation produces a periodic evoked potential in the EEG, and that the frequency characteristics of this periodic wave can be predicted by using simple linear superposition.

Further rationale for using this approach in neurofeedback includes the observation that transient evoked potentials exhibit correlations with attention and mental task. For example, evoked potentials show systematic differences in clinical populations, particularly with regard to ADD and ADHD. These findings are consistent with the understanding that the speed of cortical response is one factor that determines the frequency distribution of an EEG rhythm.

The relationship between late ERP components and endogenous rhythms becomes clear if one considers the commonalities, as well as the differences, between evoked and intrinsically generated conical activity. In the case of endogenous rhythms, interaction between the cortical centers and the thalamic nuclei produce interactive sequences of afferent and efferent bursts, which are accompanied by sequences of cortical responses. In essence, an endogenous rhythm consists of a train of "intrinsic evoked potentials," which are elicited by thalamocortical interaction, rather than by sensory stimulation. A sensory evoked potential, on the other hand, consists of the canonical response to a particular sensory input that is specified in time. In both cases, the frequency characteristics of the individual cortical responses become manifested in the power spectral density of the resulting EEG wave. Since later components of individual cortical responses produce lower frequencies in the composite power spectrum, it is reasonable to expect a cortex that produces increased or delayed late components in a sensory evoked potential to also show increased energy in low frequencies in endogenous EEG activity.

However, sensory evoked potentials are—difficult to measure because they represent the activity of only a small portion of the cells producing surface potentials, and are thus buried in background EEG noise. The duration of a typical visual or auditory evoked potential does not exceed one second, and only the early part, which comprises the first 250 milliseconds, is consistently repeatable. The later parts may vary considerably within subjects from moment to moment, and have been found to depend strongly on stimulus meaning, uncertainty, and other interpretive factors. Some form of signal-to-noise improvement is therefore necessary, and this implies a time delay for the gathering and processing of a large number of noisy responses in order to provide an evoked potential estimate in which the noise level has been reduced.

Evoked potentials are generally measured by averaging, and this requires one to two minutes for the acquisition of a single wave estimate. Since ongoing brain processes may produce evoked potential changes in mere seconds, averaging does not provide a suitable means of studying dynamic changes in brain activity. This is because the raw responses must be measured over a period of many seconds or minutes; during this time, changes due to attention, alertness, or other short-term modulations cannot in themselves be measured. On the contrary, such changes introduce signal variance which further degrades the accuracy of the final evoked potential estimate.

Several techniques are available for measuring evoked responses in a more rapid manner. One which is well suited to real-time brain monitoring is synchronous filtering of steady-state evoked potentials. By combining repetitive stimulation with synchronous filtering, it becomes possible to monitor the changing of the evoked wavelets over shortened time periods, as limited by the filtering response time-constant. This technique has the capability for rapid and ongoing measurement of evoked activity, and can respond accurately to show changes occurring over periods as short as five seconds. However, this technique has only been explored from a purely psychophysical standpoint; its application to cognitive monitoring is as of yet unexplored.

SUMMARY OF THE PRESENT INVENTION

The present invention overcomes these and other deficiencies of the prior art, by providing a method of using repetitive visual and auditory stimulation in the context of EEG neurofeedback protocols. The invention provides real-time measurement and feedback of evoked potentials in response to sensory/perceptual processes. The method is based upon an understanding and use of the fact that the EEG response is comprised of a succession of sensory evoked potentials, representing a genuine linear signal. The method is especially advantageous in that the experimental data collected shows that short-term variations in signal amplitude are shown to be sensitive to attentive state, and to reveal moment-to-moment changes in brain responsiveness.

In accordance with one general aspect of the invention, there is provided a method of using repetitive stimulation in conjunction with EEG neurofeedback protocols. Electrodes are placed on a subject's scalp. Then visual and/or auditory stimuli is displayed to the subject. Generally, the visual stimuli is in the form of flashing or square-wave light and is typically presented to the subject via goggles which the subject wears. Typically, the auditory stimulus is in the form of repetitive clicks and is presented to the subject simultaneously with the light stimuli or independently. The electrodes then transmit an electroencephalographic (EEG) signal from the subject while the stimuli is being displayed. The resultant EEG signal is then sent to a filter and filtered at a predefined frequency. The output from the filtered EEG signal is then sent to a display monitor and screen images are recorded. The EEG signal is then analyzed and monitored for short-term state changes.

In a particular embodiment of the invention, there is provided a method of measuring sensory and perceptual mechanisms and training these pathways with feedback. The method is basically the same as above, with the addition of the total evoked brain activity being reconstructed by combining the filter outputs. This evoked response can then be fed back, in real-time, to the subject. Thus, the feedback reflects the brain's response to the repetitive stimulation, and allows the subject to receive real-time feedback regarding their current state of attention.

These and other aspects of the present invention are herein described in further detail, with reference to the accompanying Figures, the illustrated embodiments being representative of only some of they ways in which the principles and concepts of the invention can be executed and employed.

DETAILED DESCRIPTION OF PREFERRED AND ALTERNATE EMBODIMENTS

The present invention provides a method of measuring evoked potentials in response to sensory/perceptual processes. Repetitive stimulation introduces a periodic evoked response in the EEG that can be measured and fed back in real time. The EEG response to repetitive stimulation can be described as a series of successive evoked potentials (EP), giving rise to a periodic response in the cortex, referred to as the steady-state visual evoked potential (SSVEP). The method is especially advantageous in that experimental data collected shows that short-term variations in signal amplitude are shown to be sensitive to short-term shifts in attention, and to reveal moment-to-moment changes in brain responsiveness.

Figure 1A:
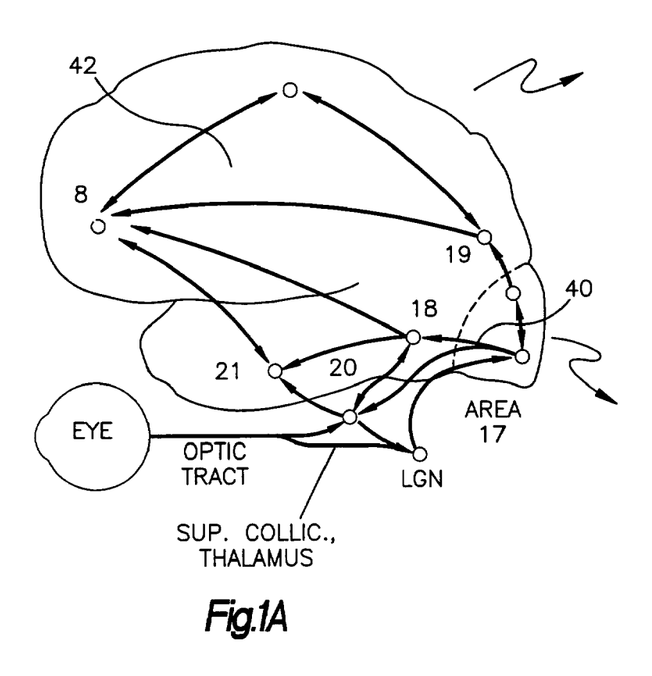
FIG. 1A is a perspective view of the neuroanatomical pathways involved in the human brain's response to a visual stimulus.
Figure 1B:
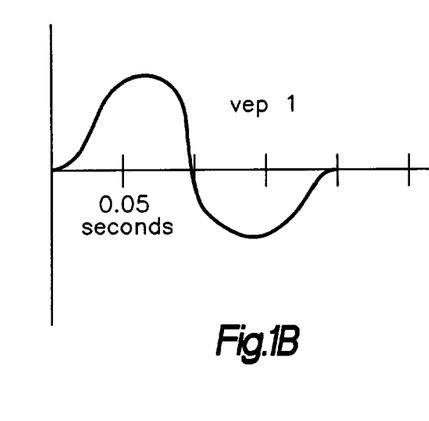
FIGS. 1B and 1C are plots of visual evoked potential brainwaves.
Figure 1C:
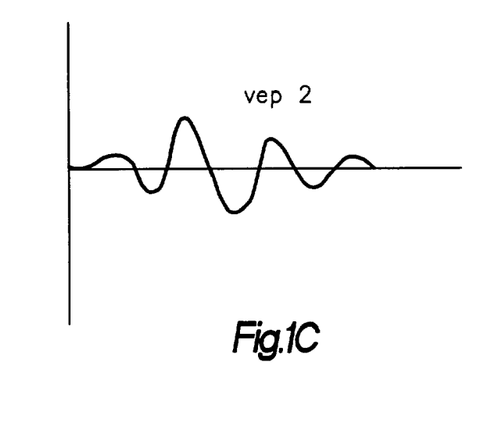

FIG. 1A depicts the neuroanatomical pathways involved in the response of the human brain to a light flash. When neural activity first reaches the visual cortex 40, the early components of the visual evoked potential are produced. As activity diffuses in the cortex and reaches the association areas 42 of the brain, the later components of the evoked potential are produced. FIGS. 1B and 1C are wave plots representative of measured VEP brainwave signals.

Figure 2A:
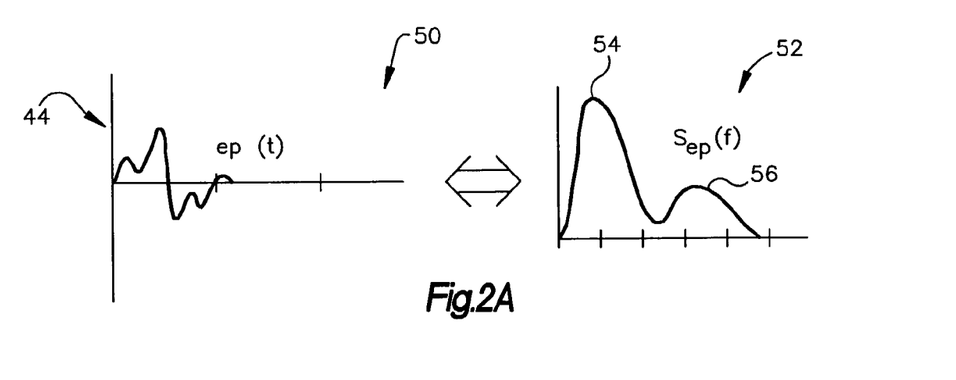
FIGS. 2A–2C depicts the signal and frequency spectral properties of a visual evoked potential (VEP), a repetitive stimulus train, and the resulting steady-state visual evoked potential (SSVEP) respectively.
Figure 2B:
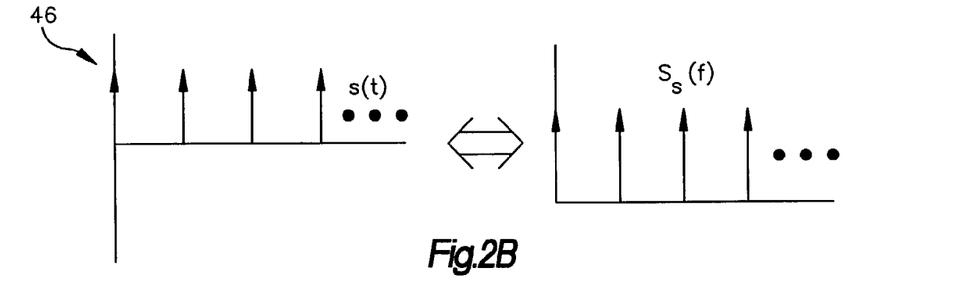
Figure 2C:
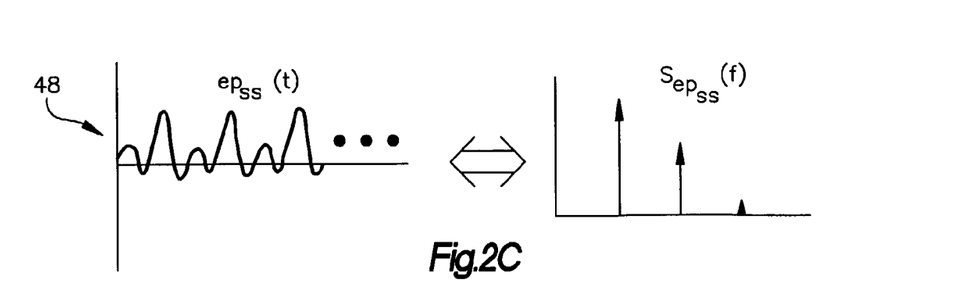
Figure 3A:
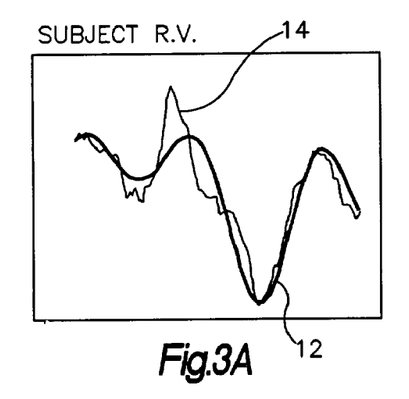
FIG. 3 depicts the SSVEP (real-time) waveform superimposed on the averaged VEP waveform.
Figure 3B:
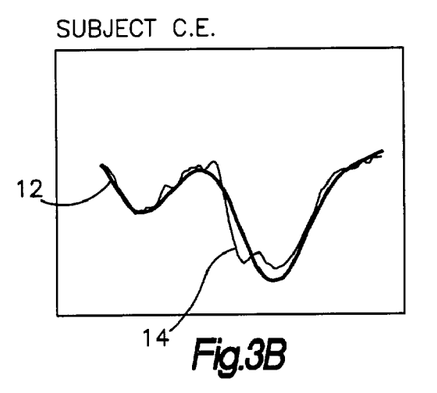
Figure 3C:
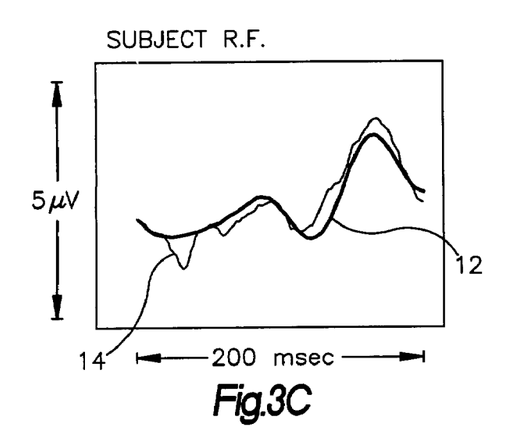
Figure 3D:
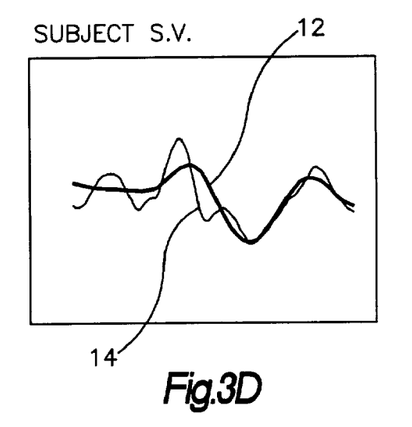

FIGS. 2A–2C illustrate the principle by which evoked potential energy is produced at the appropriate frequencies, whenever a repetitive, pulse-like stimulus produces a train of responses. The signals depicted are for an 8.5-per-second visual stimulus rate, with the top trace 44 representing the signal and frequency spectral properties of a visual evoked potential (VEP), the middle trace 46 representing the repetitive stimulus train, and the bottom trace 48 representing the resulting steady-state visual evoked potential (SSVEP). Traces 50 represent time-domain signals, and Traces 52 represent the corresponding frequency spectra. Thus, Traces 52 are Fourier Transforms of the corresponding traces 50. Therefore, the bottom left signal (FIG. 2C) is the convolution of the two signals above it (FIGS. 2A, 2B), while the bottom right spectrum (FIG. 2C) is the product of the two spectra above it (FIGS. 2A, 2B), due to the convolution theorem of the Fourier Transform. This analysis explains the observed EEG spectral peaks at the fundamental and harmonic frequencies, when a repetitive visual stimulus is presented. In the case of visual evoked potentials, two predominant energy bands are observed, one from 4 to 10 Hz (54), the other from 15 to 20 Hz (56). Therefore, by providing visual stimulation at the rate of 8.5 per second and filtering at 12 Hz and at 17 Hz, it is possible to estimate the energy in each of these components separately, and in real time.

The SSVEP is recorded by filtering the EEG using narrow-band filters (not shown). The filters are designed with center frequencies that match the stimulus frequency, and its integral harmonics. This provides the ability to measure the signal components in real-time. By reconstructing the periodic waveform from its harmonic components, the entire SSVEP can be estimated. This method focuses on analyzing the EEG components that are locked to the stimulus, and is designed to reject other activity. Thus, this method does not attempt to determine any effects that the stimulation has on intrinsic rhythms or background activity. Instead, it focuses on measuring the response to the stimulation only, thus reflecting sensory/perceptual activity both from primary sensory areas, and also any broader cortical late activity that may also be stimulus-locked.

In order to record evoked potentials in this manner, we stimulate at the rate of F flashes per second, and then filter the EEG at 1F, 2F, 3F, and so on. All of the recordings shown here were measured using specially constructed analog filters of the quadrature ("hererodyne") type. The SSVEP can be measured in real time, and it could be fed back, permitting the trainee to hear the visual cortex as it responds to the lights that are being seen. In the studies shown here, there was no feedback to the trainee.

Subjects in this study were four normal males of college age. They were screened to insure that none had a psychological or neurological disorder, including epilepsy or ADD. Example data was recorded during a single session for the 4 Hz studies, and another session for the 7.5/8.5 Hz studies. Data shown are typical, and are illustrative, being from single trials of the methods described below.

Visual stimuli were presented using yellow LED's mounted in welder's goggles positioned over the subject's open eyes. LED's were positioned to achieve visual overlap ("fusion") of the two spots. LEDs were driven by 10-millisecond current pulses, providing an averaged light output of 0.0023 milliwatts per eye. A Grass silver chloride electrode was placed at Cz, referenced to the right ear, with a left ear ground. EEG was measured using a Grass Model 12 EEG amplifier (type 7P511) with bandwidth set at 0.1 to 30 Hz. This signal was fed into channel 1 of a Hewlett-Packard Signal Averager, which was set to average 64 successive responses. The signal was also sent to a custom-built comb filter that filtered the EEG at 4, 8, 12, and 16 Hz, using third-order analog filters (Butterworth type). The time-constant of the filters was set at 2.5 seconds. This provided an effective bandwidth of 0.13 Hz, which is sufficient to reject unrelated EEG activity, while responding quickly to changes in the evoked responses. The output of this filter was fed into channel 2 of the Signal Averager for display, where it could be superimposed on the averaged signal computed within the instrument. Channel 2 was not averaged, however. As channel 1 was collected and averaged, channel 2 was set to free-run, providing a single sweep display that synchronized the two signals for visual comparison. Screen images were captured using a Polaroid camera attached to the bezel of the Averager.

As an alternative presentation, time-series were recorded on a Gould Model 2400 4-channel strip chart recorder. All 4 banks of the comb filter were summed into one channel of the strip chart, to reveal the composite SSVEP as an ongoing waveform. This was plotted simultaneously with the raw EEG signal, for visual comparison.

When monitoring short-term state changes, visual stimulation of 8.5 flashes/second was used. Auditory stimulation (clicks) at 7.5 per second was also presented, as an alternative target for the subject's attentive focus. Clicks were produced by providing 1.4 volt peak-to-peak pulses to AKG K 140 stereo headphones. EEG was fed into the comb filters described above, with center frequencies set at 7.5, 15, 8.5, and 17 Hz. The output of the comb filters was fed into a Gould Model 2400 4-channel strip chart recorder that used pen-and-ink to record the traces on moving paper. These traces provide a continuous readout of the filter signals. The chart speed was slowed so that one page of data covered 2 minutes. Because the traces run slowly, the sinusoidal filter outputs draw a solid area that describes the amplitude (envelope) of the signal. For the 7.5/8.5 Hz recordings, individual filter channels were fed to separate traces, so that they could be seen independently.

Typical results of the 4 Hz study, including a comparison with the averaged VEP, are shown in FIGS. 3A–3D. What is seen is the response of the brain to a light flashing four times per second. There are two traces superimposed on each of the four graphs. One trace 12, the smoother of the two, is the "free running" output of the bank of filters set at 4, 8, 12, and 16 cycles per second. Superimposed on each of these filter responses is the average evoked potential 14, computed by the signal averager.

The responses in FIGS. 3A–3D exhibit the familiar ERP components, including the usual positive and negative transitions. The filter outputs are seen to superimpose on the average evoked potential 14 demonstrating that even as we begin to flash repetitively, the resulting wave is a composite evoked potential. During the time that the average is being computed, the filter output was seen to change in shape, as is also evident in FIG. 4. For example, the trace of FIG. 3D (Subject S.V.) shows two leading peaks at approximately 40 and 80 milliseconds in the average, but only one (at approximately 90 milliseconds) in the SSVEP. However, during this acquisition, both peaks were observed in the SSVEP to wax and wane, and also to change in latency, in the final SSVEP sweep which is the one shown on the display, only the 80 millisecond peak happened to be evident. This illustrates that the SSVEP is capable of dynamically tracking latency (and amplitude) changes that are obscured in the averaged EP, because the averaged EP combines changing features into a single waveform that represents the entire acquisition period. When the average is complete, the screen depicts the final sweep of the filter output, which is an estimate of the most recent SSVEP wave. These time variations are seen more clearly in a continual waveform display, as follows.

Figure 4:
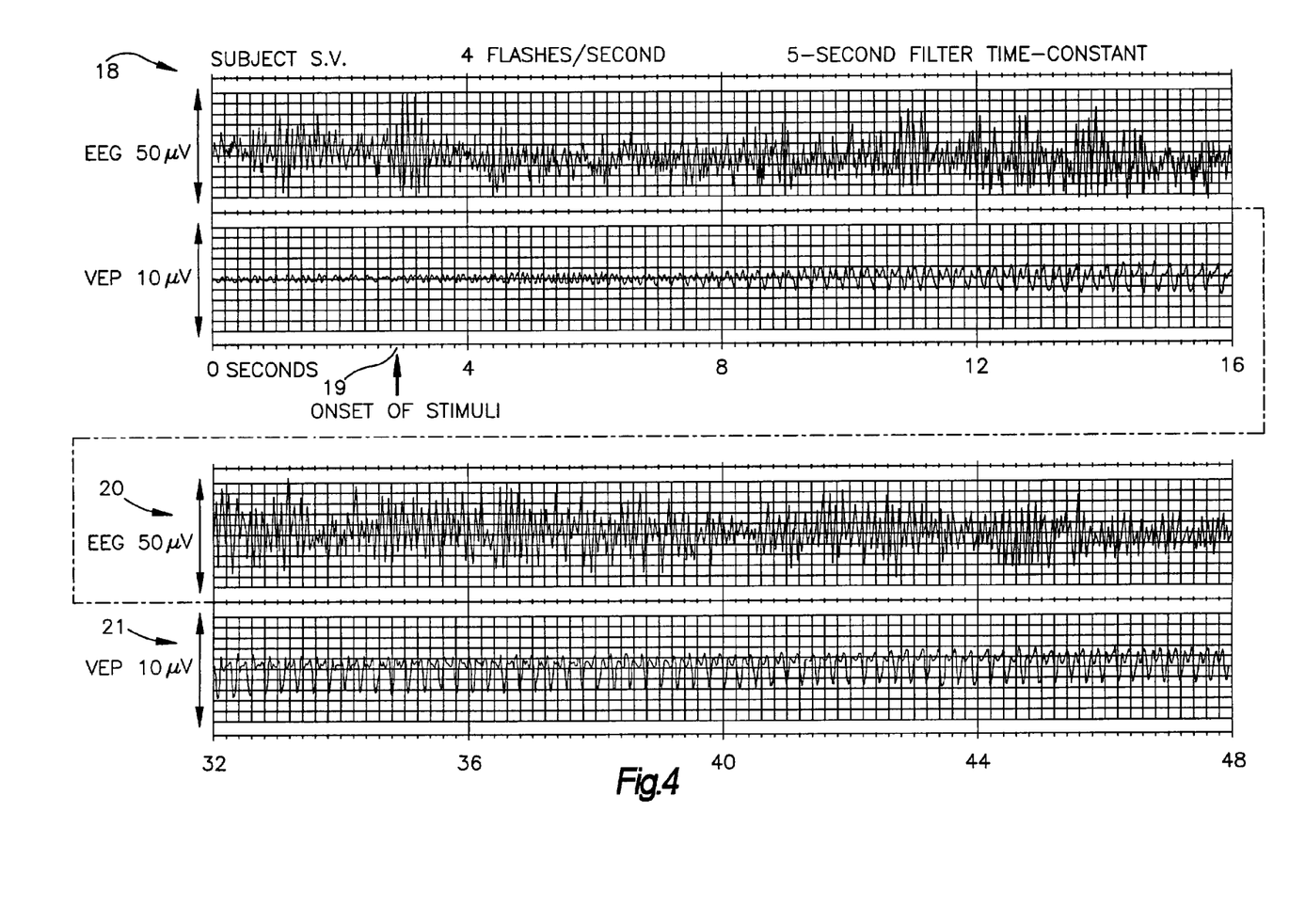
FIG. 4 depicts a pair of 16-second traces of the EEG waveform.

FIG. 4 depicts a subject with an EEG trace running across the top of each pair and the combined output of the filters beneath it. It has been seen that the output of the filters is in fact a good estimate of the evoked potential that would be measured with an averager. The benefit of this technique is that the SSVEP is measured in real time, based upon the properties of the filters. Along the upper trace 18, we have the first 16 seconds of the recording. Before the stimulus is presented, the filters have a small output, as seen on the beginning trace. The stimulation 19 is turned on 3 seconds into this trace. By the time 16 seconds are over, the filters are already producing a very good estimate of the evoked potential. This SSVEP signal consists of a continual series of SSVEP waves that are the same as one trace of FIGS. 3A–3D, only shown concatenated in time. The start of each SSVEP wavelet is synchronized with the light flash that is occurring 4 times per second. If this trace is magnified, it produces an estimate of the waveform that would be obtained from signal averaging. However, instead of waiting a minute or more to see an estimated averaged VEP, it is possible to see the SSVEP result in real time. This output reveals the connection between the transient evoked potential wave morphology, and the complex SSVEP wave that consists of the fundamental plus harmonics of the stimulus rate.

On the bottom trace 20 that extends from 32 seconds to 48 seconds after stimulus onset, even though the stimulation period has not approached one minute, visible changes are evident. Careful inspection reveals a fine detail in the evoked potentials, and one can identify particular peaks and valleys with particular latencies and amplitudes. These features can be seen changing about every 4 or 5 seconds. This method thus allows us to probe the brain functionally, allowing us to see what is occurring live, and in real time. This is much different from signal averaging, which provides a single, static wave estimate, after a minute or two. The real-time ability of this technique opens the door to doing biofeedback on this type of a response. This is, therefore, EEG evoked potential neurofeedback, and can be performed in real time.

Figure 5:
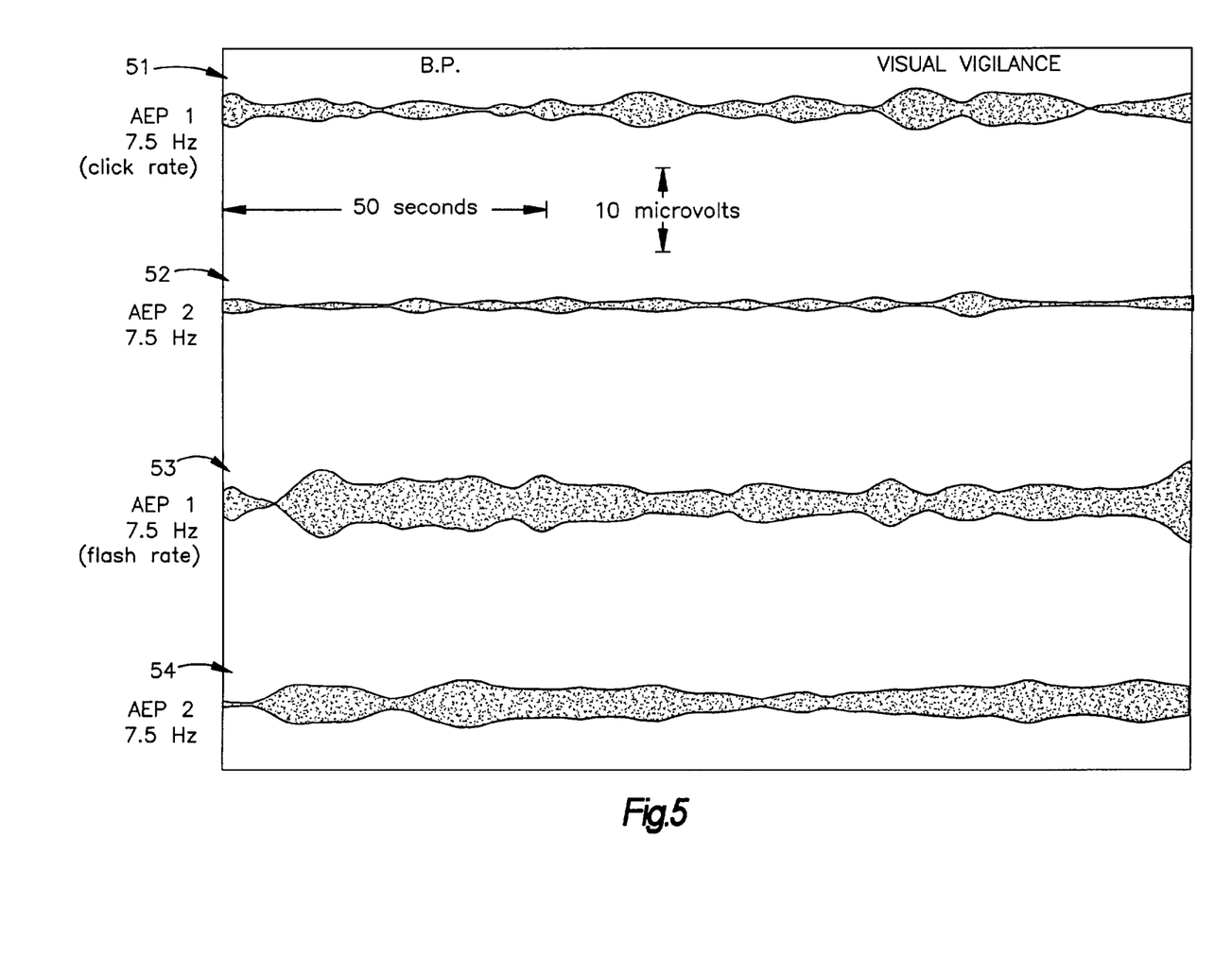
FIG. 5 depicts the auditory and visual responses for SSVEP evoked-potential envelopes recorded during a visual vigilance task.
Figure 6:
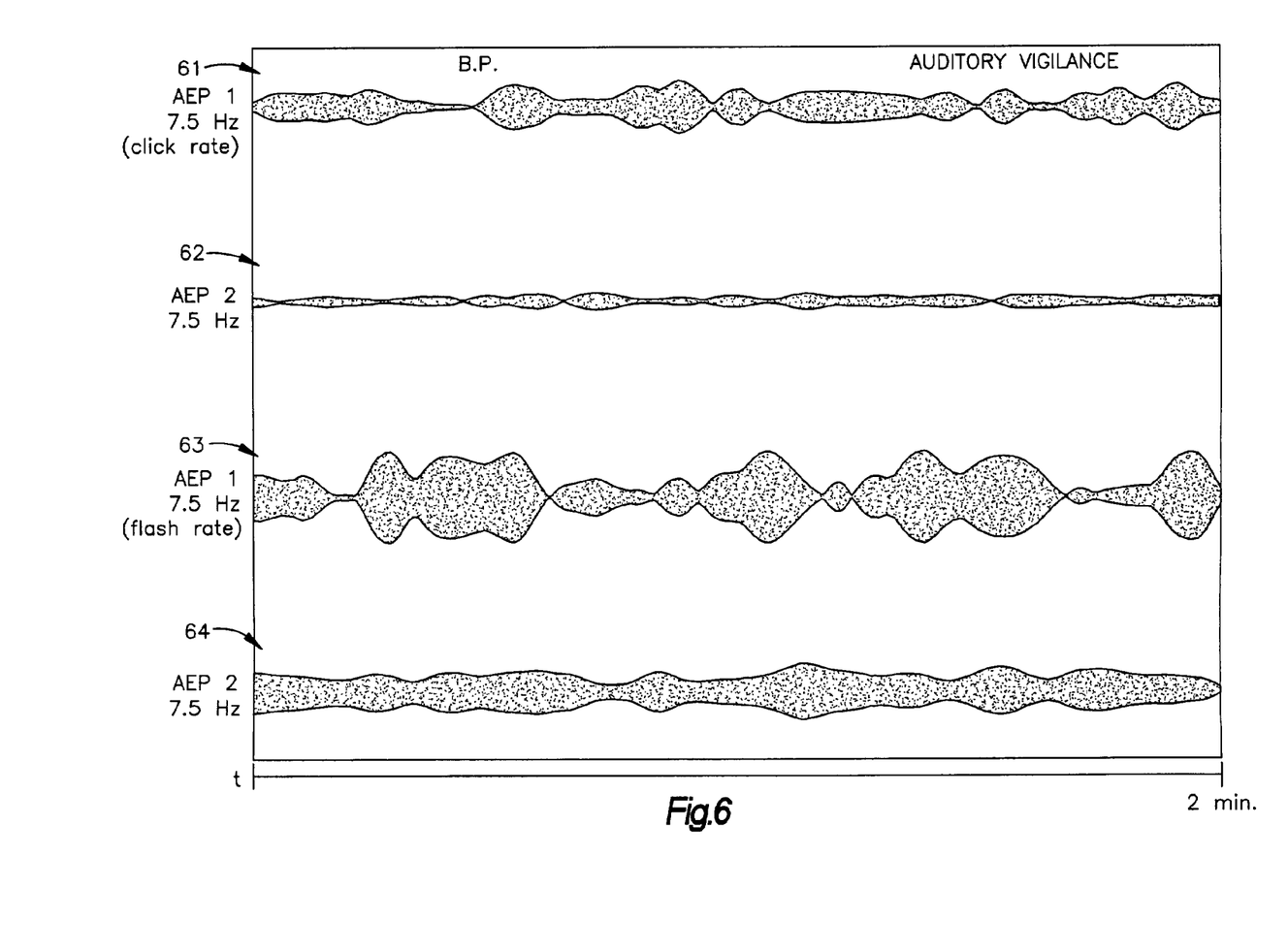
FIG. 6 depicts the auditory and visual responses for SSVEP evoked-potential envelopes recorded during a auditory vigilance task.

FIGS. 5 and 6 illustrate short-term variations in signal amplitude under two different task conditions. As an example of short-term variations in SSVEP component amplitudes, FIG. 5 shows filter outputs during the case of visual vigilance. In this example, the trainee is performing a visual vigilance task, and is pressing a button whenever a small (less than 3 dB) change is seen in the visual stimulus. The two upper traces 51 and 52 show the filtered activity associated with auditory stimulus (clicks), used as an alternative attentive target for the vigilance task. Observing the lower two traces 53 and 54, we see the visual evoked potential at the primary frequency, which happens to be 8.5 Hz. Beneath this is the secondary component at 17 Hz. Visually, a candlestick type of appearance is evident, reflecting the characteristic waxing and waning of the signal amplitude. A moment later, the subject performs the corresponding auditory vigilance task (FIG. 6). There is a visible difference in the time-course of the evoked potentials seen in traces 63 and 64, while no such difference is seen in traces 61 and 62. The entire time here is about two minutes. One can actually see the changes in how the brain responds moment to moment. In the case of auditory vigilance the visual cortex appears to be much more labile, with much more waxing and waning in trace 63, while trace 64 is larger, but just as steady as before. Based upon our earlier considerations, these results suggest that the observed variations occur in the attentional pathways that produce the later (lower frequency) components, rather than in the sensory/perceptual pathways that produce the earlier (higher frequency) components. This thus provides a very selective mechanism, by which we can selectively feed back (and train) the neural pathways of interest, exploiting the signal characteristics as a way to pinpoint the neuroanatomical mechanisms we wish to affect.

We have seen that the response to flashing stimuli produces energy at the fundamental and harmonies of the stimulus rate, and that this is a simple outcome of the generation of a complex periodic wave, which is the SSVEP. It is thus possible to interpret real-time filtered SSVEP data in light of the corresponding EP model. Consider the case with 8.5 stimulation. The response to 8.5 Hz flash represents the energy in the low-frequency band, and the 17 Hz response represents the energy in the high-frequency band. We are, in effect, sampling the amplitude of the EP frequency spectrum, by performing repetitive stimulation and filtering the corresponding components from the raw EEG. We observe these responses to wax and wane independently, suggesting independent generators in the brain. This is interpreted as the high-frequency response reflecting primary sensory mechanisms that produce short-latency EP components (less than 120 msec), while the low-frequency response reflects secondary mechanisms that produce longer latency (between 150 and 250 millisecond) components. We are thus able to separate, in frequency, the brain processes that conventional EP averaging endeavors to perform in the time domain.

The appearance of harmonies in this case is not due to any non-linearity in the brain. They appear due to the simple signal properties of creating a repetitive signal, which is not just a simple sine wave. The measured EEG response of the brain is what would be predicted if the responses to a slower flash are sped up. Electrophysiologically, there is no evidence for any entrainment or EEG driving in this case. Entrainment is a nonlinear, plastic process that would produce 1) larger than expected evoked responses, and 2) lasting EEG changes after the withdrawal of the stimulus, hopefully for a long period of time.

The observed "resonance" at "alpha" is in fact an EP response maximum that happens to occupy the same frequencies as low alpha (7–9 Hz). This SSVEP response peak is predictable based upon the morphology of single EP's, and the presence of a spectral energy maximum at this range, because the EP itself contains appreciable signal components in the 120 to 140 millisecond range.

The invention provides a method to record, measure, and train the sensory pathways that are associated with the evoked activity itself, and to produce EEG systems that are able to control visual stimulation as an assist to neurofeedback, without being restricted to specific frequency or entrainment-based approaches. The evoked-potential-based approach appeals to a different set of physiologic considerations, involving the learning processes in sensory-related pathways, and interactions between them. These interactions define the nature of the induced SSVEP activity, as well as short-term variations in the evoked responses.

Figure 7:
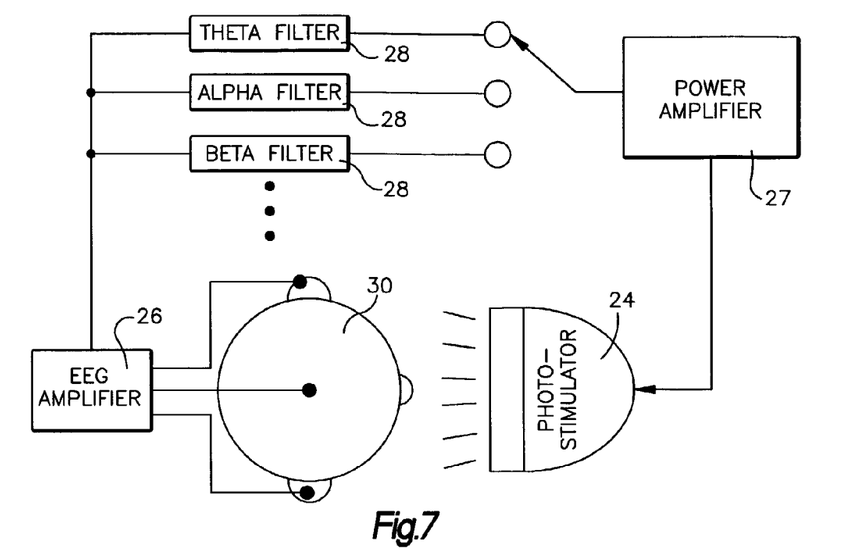
FIG. 7 is a schematic view of the basic system for nonvolitional EEG biofeedback.

At the simplest level, photic stimulation can be used with EEG neurofeedback, as a simple adjunct. This might precondition an individual before training, or postcondition them afterwards. This is not integrated with the neurofeedback. This could used before, during, or after neurofeedback, but it is not controlled by the EEG in any way. However, using the EEG to control the stimulus parameters offers additional possibilities. One method is called non-volitional EEG neurofeedback, as shown in FIG. 7. In this method, the EEG signals transmitted to the EEG amplifier 26 are filtered through various theta, alpha and beta filters 28 and recorded. Then, the EEG is used to control a stimulator 24, Through an amplifier 27, to train an increase in the evoked response. This approach can also be used to decrease a rhythm.

Figure 8:
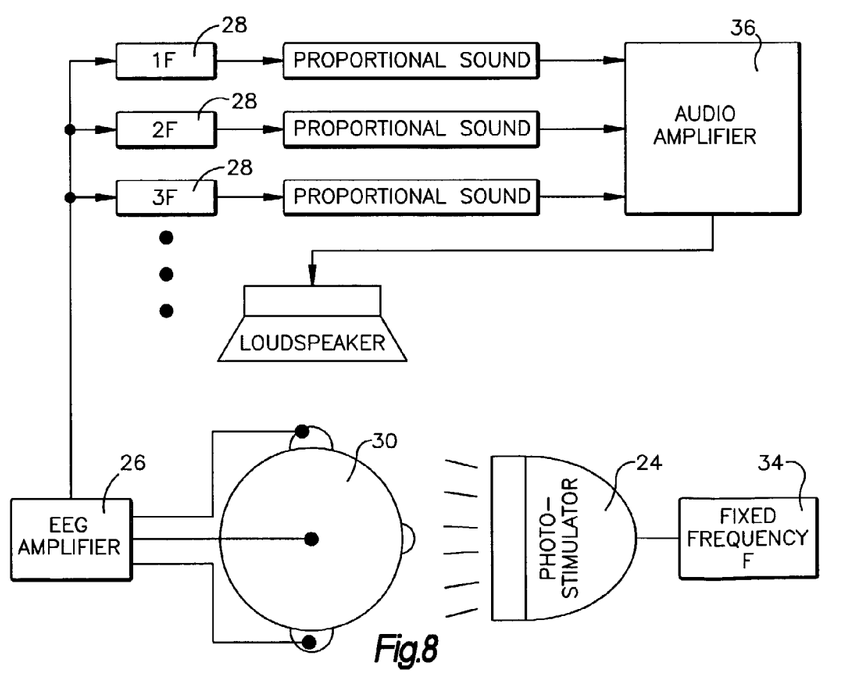
FIG. 8 is a schematic view of the basic system for SSVEP biofeedback.

FIG. 8 illustrates one approach to using the SSVEP signal itself for feedback. In a system of this type, the EEG signals are transmitted to the EEG amplifier 26 and filtered 28, as before, but now the trainee 30 hears the brain's sensory/perceptual response mechanisms in real time via an audio amplifier 36, and can use these for training purposes. The audio feedback reflects the brain's response to the repetitive stimulation, and allows the trainee 30 to receive feedback regarding their current state of attention. This trains different pathways and mechanisms than conventional neurofeedback. It actually trains the sensory/perceptual pathways based upon evoked activity, using a volitional technique.

One can make a distinction between volitional and non-volitional methods using this approach. A volitional method requires instructions to the trainee, and presupposes expectation of a reward or a goal. The feedback provides information that must be rapid, accurate, and aesthetic. The trainee must find and recognize states reflected in the feedback information, consciously or unconsciously. Learning occurs with practice under an operant conditioning model, and generally produces lasting effects.

In non-volitional methods, on the other hand, there are no instructions to the trainee and the stimulus itself introduces a state or a change in a state. It may introduce the brain to a state, or it may remove the brain from a state. One example of this is theta blocking described previously. In this case, the effect of the stimulation does not depend on instructions to, or the intent of, the trainee. In time, the trainee may become more accustomed to being in a different brain state. This type of learning is closer to classical conditioning than operant conditioning.

In all of these examples, regardless of volitional or nonvolitional aspects of the neurofeedback design, the direct effect of the stimulus on the EEG is transient, and disappears once the stimulation is withdrawn. It is thus possible to introduce the brain to a frequency experience, and after a brief period of this experience, discontinue the stimulation. Such methods may reduce neurofeedback training times, but do not depend on any determination of the dominant EEG frequencies, or appeal to any nonlinear entrainment phenomena. When volitional and non-volitional neurofeedback is combined, it is possible to produce a more rapid initial ramp-up to the learning process. This can provide an ongoing assist ("training wheels"), or assist with difficult aspects, for example, a trainee having difficulty with theta reduction. This can provide more aggressive reduction of undesirable rhythms, can introduce the brain to particular states, and may combine such effects, in a single neurofeedback protocol.

Non-volitional aspects can be added to the volitional neurofeedback, which may have significant effects. Specific brain pathways and mechanisms can be probed by the described method.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive. Other features and aspects of this invention will be appreciated by those skilled in the art upon reading and comprehending this disclosure. Such features, aspects, and expected variations and modifications of the reported results and examples are clearly within the scope of the invention where the invention is limited solely by the scope of the following claims.

What is claimed as the invention is:

1. A method of measuring sensory and perceptual mechanisms of the brain, and training these mechanisms with feedback, comprising the steps of:
   securing electrodes to a subject's scalp;
   displaying stimuli to the subject;
   receiving an electroencephalographic (EEG) signal from the subject while the stimuli is being displayed;
   transmitting the resultant EEG signal to a filter;
   narrow band filtering the EEG signal to a predefined frequency;
   reconstructing the total evoked brain activity by combining the filter outputs;
   feeding back in real-time of the total evoked response comprising at least one steady-state visual evoked potential (SSVEP) component amplitude; and
   monitoring, in real-time, the short-term changes in each of the SSVEP component amplitudes, for the interpretation of waxing and waning behavior to reflect variations in sensory and perceptual vigilance for use as criteria for providing feedback for at least one of training, monitoring, and assessment purposes.

2. The method of claim 1 wherein the EEG signal is used to control a stimulator which produces a visual stimulus, wherein the control trains an increase or decrease in the evoked response.

3. The method of claim 1 wherein auditory feedback consisting of heard sounds is employed to reflect to the subject the subject's brain response to the applied visual, wherein the feedback trains the sensory/perceptual pathways of the brain.

4. The method of claim 1 wherein the subject receives, in real-time feedback specific to particular sensory and perceptual pathways of the brain, and receives feedback, of evoked-potential components that differentially reflect waxing and waning of independent generators in the brain, with real-time information facilitating operant or learned (volitional) conditioning of the brain.

5. The method of claim 1 wherein particular components of the SSVEP are extracted in real-time and used to make a control decision that can result in either a change in feedback, an automated decision, a switch closure, the triggering of an actuator, or another event.

6. The method of claim 1 wherein the composition of harmonic activity in the SSVEP is used in real-time to provide variations in an auditory feedback signal, so that the trainee hear, separately, the brain's visual primary and secondary sensory and perceptual response mechanisms in real time via an audio amplifier for training purposes.

7. A method of measuring sensory and perceptual mechanisms of the brain, either separately or together, and training these mechanisms with feedback, comprising the steps of:
securing electrodes to a subject's scalp;
displaying stimuli to the subject;
receiving an electroencephalographic (EEG) signal from the subject while the stimuli is being displayed;
transmitting the resultant EEG signal to a filter;
narrow band filtering the EEG signal to a predefined frequency;
reconstructing the total evoked brain activity by combining the filtered waveform outputs;
feeding back in real-time of the total evoked response comprising a steady-state visual evoked potential (SSVEP) waveform; and
reconstructing, in real-time, an estimate of the SSVEP waveform using the combined filtered waveform outputs for dynamically tracking latency and amplitude for the measurement of sensory and perceptual mechanisms of the brain.

8. The method of claim 7 wherein the EEG signal is used to control a stimulator which produces a visual stimulus, wherein the control trains an increase or decrease in the evoked response.

9. The method of claim 7 wherein auditory feedback consisting of heard sounds is employed to reflect to the subject the subject's brain response to the applied visual, wherein the feedback trains the sensory/perceptual pathways of the brain.

10. The method of claim 7 wherein the subject receives, in real-time feedback specific to particular sensory and perceptual pathways of the brain, and receives feedback, of evoked-potential components that differentially reflect waxing and waning of independent generators in the brain, with real-time information facilitating operant or learned (volitional) conditioning of the brain.

11. The method of claim 7 wherein particular components of the SSVEP are extracted in real-time and used to make a control decision that can result in either a change in feedback, an automated decision, a switch closure, the triggering of an actuator, or another event.

12. The method of claim 7 wherein the composition of harmonic activity in the SSVEP is used in real-time to provide variations in an auditory feedback signal, so that the trainee hears, separately, the brain's visual primary and secondary sensory and perceptual response mechanisms in real time via an audio amplifier for training purposes.

* * * * *